(12) United States Patent
Lokshin et al.

(10) Patent No.: US 9,326,704 B2
(45) Date of Patent: May 3, 2016

(54) METHOD AND APPARATUS FOR DETERMINING SPORTSMAN JUMPS USING FUZZY LOGIC

(75) Inventors: Anatole M. Lokshin, Huntington Beach, CA (US); Vitaly Kuzkin, Saint Petersburg (RU)

(73) Assignee: AlpineReplay, Inc., Huntington Beach, CA (US)

(*) Notice: Subject to any disclaimer, the term of this patent is extended or adjusted under 35 U.S.C. 154(b) by 711 days.

(21) Appl. No.: 13/612,470

(22) Filed: Sep. 12, 2012

(65) Prior Publication Data

US 2013/0346013 A1    Dec. 26, 2013

Related U.S. Application Data

(60) Provisional application No. 61/663,439, filed on Jun. 22, 2012.

(51) Int. Cl.
*A61B 5/11* (2006.01)
*A63B 24/00* (2006.01)
*G06F 19/00* (2011.01)
*A61B 5/00* (2006.01)
*A43B 3/00* (2006.01)

(52) U.S. Cl.
CPC ............... *A61B 5/112* (2013.01); *A61B 5/1123* (2013.01); *A61B 5/7264* (2013.01); *A43B 3/0005* (2013.01); *A61B 5/1112* (2013.01); *A61B 2503/10* (2013.01); *A61B 2562/0219* (2013.01); *A63B 24/0062* (2013.01); *A63B 2220/40* (2013.01); *G06F 19/3481* (2013.01)

(58) Field of Classification Search
CPC ............... A63B 2220/40; A63B 69/18; A63B 2069/185; A63B 24/0062; A63B 2024/0071; A63B 2071/065; A63B 2220/16; A63B 2220/44; A63B 2220/833; A63B 2244/19; A63B 5/00; A63B 71/06; A63B 2024/0025; A63B 2071/0663; A63B 2220/12; A63B 2220/51; A63B 2220/53; A63B 2220/803; A63B 2244/08; A61B 2562/0219; A61B 5/11; A61B 5/6895; A61B 5/681; A61B 5/1121; A61B 5/1123
See application file for complete search history.

(56) References Cited

U.S. PATENT DOCUMENTS

| | | | |
|---|---|---|---|
| 5,724,265 A | 3/1998 | Hutchings | |
| 5,825,667 A | 10/1998 | Van Den Broek | |
| 6,167,356 A | 12/2000 | Squadron et al. | |
| 6,445,882 B1 * | 9/2002 | Hirano | 396/52 |

(Continued)

OTHER PUBLICATIONS

Valerie Pitt, The Penguin Dictionary of Physics, p. 158, Penguin, Harmondsworth, New York (1977).

(Continued)

*Primary Examiner* — Mischita Henson
*Assistant Examiner* — Christine Liao
(74) *Attorney, Agent, or Firm* — Greenberg Traurig LLP

(57) ABSTRACT

A method and apparatus for detecting a jump of a moving sportsman and separating the jump from other sportsman motion is described. Accelerometer data generated by a sportsman's motion is received in a computing device. The computing device is used to apply fuzzy logic membership functions to a plurality of parameters associated with the accelerometer data to detect a pattern associated with jumps. A subset of the data is identified as representing a jump based upon the detection of the pattern. The determination is used in the computing device to transform data, whereby jumps are separated from other sportsman motion.

12 Claims, 5 Drawing Sheets

(56) References Cited

U.S. PATENT DOCUMENTS

| | | |
|---|---|---|
| 6,539,336 B1 | 3/2003 | Vock et al. |
| 7,640,135 B2 | 12/2009 | Vock et al. |
| 7,860,666 B2 | 12/2010 | Vock et al. |
| 2002/0052541 A1* | 5/2002 | Cuce et al. ............... 600/300 |
| 2003/0163287 A1 | 8/2003 | Vock et al. |
| 2005/0243061 A1* | 11/2005 | Liberty ............ A61B 5/1101 345/158 |
| 2009/0322540 A1 | 12/2009 | Richardson et al. |
| 2010/0191499 A1 | 7/2010 | Vock et al. |
| 2010/0204615 A1* | 8/2010 | Kyle et al. ............... 600/595 |
| 2013/0044043 A1* | 2/2013 | Abdollahi et al. ............ 345/8 |

OTHER PUBLICATIONS

"Free Fall," http://en.wikipedia.org/wiki/Free_fall.

International Patent Application PCT/US2012/071869, International Search Report and Written Opinion, Apr. 29, 2013.

\* cited by examiner

METHOD AND APPARATUS FOR DETERMINING SPORTSMAN JUMPS USING FUZZY LOGIC

This application claims priority to U.S. Provisional Patent Application Ser. No. 61/663,439, filed Jun. 22, 2012 entitled "Method And Apparatus For Determining Sportsman Jumps Using Fuzzy Logic," which is incorporated herein by reference in its entirety.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of devices for determining parameters such as time duration in connection with sporting activities, and in particular to methods and apparatuses for calculating parameters associated with jumps in such activities.

BACKGROUND

In sporting activities there are times when sportsmen perform jumps, which are characterized by continued motion through the air without mechanical assistance. Such jumps are often performed in such sports as water and alpine skiing, snowboarding, wakeboarding, motorcycling, biking, gymnastics, high jump, and others. In such sports the duration of the jump and the height of the jump are of most interest to the sportsmen and spectators.

In the past, duration of the jump has been determined by observing a sportsman in real time or carefully inspecting a video recording to determining the start and end points of a jump visually. An observer can start a stopwatch when he things that sportsman left the ground (or water) and stop the stopwatch when person appears to have landed. This method works relatively well, especially when a slow motion video recording is used and then examined frame by frame. However, such determination requires a second person making video and then a labor consuming process of manual examining video and timing motion frame by frame.

With advances in electronic sensors and computer processing power, various research has been done to detect and measure sports jumps using sensors attached to the sportsman or his equipment.

In U.S. Pat. No. 5,724,265 to Huthings, the inventor proposed to install contact sensors in a runner's shoes. When both sensors do not measure any contact, a person is determined to be in the air. In principle, such approach may be used for other sports but it is not very practical for many sports, such as skiing and wakeboarding.

Volk, et al., in U.S. Pat. No. 6,539,336 proposes to measure energy expanded by the skier and skier vibration. However, it is not clear how power can be reliably measured and how it is related to airtime.

With advances in accelerometer sensors, a much more efficient method of air time determination became possible. During the jump, the only forces imposed upon sportsmen are generally Earth gravity and air resistance. For the terrestrial and water sports, such as snowboarding, bike jumps, wake boarding, etc., the air resistance is very small, therefore, this motion can be considered as a "free fall", as is disclosed in *Dictionary of Physics*, Vi edited by Valerie H. Pitt, Penguin, 1977. This is true even when the body actually moves upward at the initial stage of the jump. Alternatively, during skydiving, the jumper quickly reaches so called 'terminal velocity" where air resistance becomes equivalent to the force of gravity and cannot be disregarded. See the article "Free Fall," http://en.wikipedia.org/wiki/Free_fall.

It is well known according to the laws of physics that, during free fall, an accelerometer sensor that is attach to that body should show zero signal in any direction. See the article "Free Fall," http://en.wikipedia.org/wiki/Free_fall. This is also known from various physics textbooks. Therefore, to detect a free fall is essentially the same as to determine that all accelerometer signals are zero. However, this fact, while well known theoretically, is not so easy to realize in a real world practical situation.

Vock, et al., in U.S. Pat. No. 7,640,135, teach that free fall should be detected when " . . . summing acceleration signals from the tri-axial accelerometers, wherein the acceleration signals sum to zero when the sportsman is in free-fall." Unfortunately, real world signals rarely sum up to zero due to sensor noise and sensor calibration errors. The same inventors disclose improved criteria in U.S. Pat. No. 7,860,666, wherein it is proposed that, instead of looking for a virtual zero signal, the signal should be compared with a predefined threshold on the acceleration signal value. In particular, the patent discloses " . . . determining a period of free-fall comprising timing a duration of acceleration signals below an acceleration floor, wherein acceleration signals above the floor indicate an end to the free-fall period."

Again, real world situations often do not allow the selection of one accelerometer value which sufficiently separates jumps from non jumps. FIG. 1 presents accelerometer data collected by a skier during a downhill run with jumps. For data collection a smart phone with built in accelerometers and GPS was used. The phone was kept in a breast pocket of the skier's jacket during the run. The jumps were performed near sample number 500 and near sample 800. FIG. 1 presents a sum of tri-axis accelerometer during this run. It is clear that while there are two jumps performed during this sample period, there are no samples in this segment where sum of 3-axis acceleration is equal to zero or even very close to zero. It is also clear that even within a jump the acceleration value could vary significantly and a single threshold would not allow a reliable detection. This is due to several factors.

Firstly, accelerometers have noise and bias, and if not well calibrated, can generate erroneously large readings. Secondly, the sum of acceleration signals could be small when individual directions have large but opposite sign signals. Another source of large acceleration during jump could be skier rotation. During rotation, accelerometers measure centrifugal acceleration that can be significant. Another possible reason is that very often a measuring device is not rigidly connected to the skier or his equipment but is a free standing device, such as when a smart phone with GPS and accelerometer sensors is used. Such device can be loosely positioned in a pocket and move independently on the user, registering additional shocks when bumping around inside the pocket.

In addition to the use of amplitude of individual accelerometers to detect free fall, U.S. Pat. No. 7,640,135 teaches that free fall can be detected when acceleration signals are changing at a low frequency relative to the high frequency acceleration signal that is generated during motion over ground or water. Similarly, Vock et al., in U.S. Pat. No. 7,860, 666, use the absence of high oscillation to detect and measure air time by " . . . processing the accelerometer data comprising determining an absence of vibration to identify loft of the sportsman". Vock et al. suggest using a microphone to record vibration and determining "loft" by the absence of such vibration in the microphone signal.

Unfortunately, many real world situations are more complicated. FIG. 2 shows accelerometer data used in FIG. 1. As can be seen in FIG. 2, the acceleration signal during jumps has a frequency comparable to such signal during non jump motion. In some real world situations "low frequency acceleration" criteria often does not work and leads to non-detection or false-detection of significant jumps.

One of the characteristic parameters of a jump should be a presence of a landing shock when all the energy of the flight must be quickly absorbed. While landing shock is a very attractive concept, in practice it needs to be detected and measured in order to be useful.

Another problem is that other activities, e.g. walking, produce accelerometer signals that by many characteristics appear very similar to the signals recorded during ski or other sport jumps.

FIG. 3 presents acceleration data collected during a walk, with accelerometer sensors kept in a pants pocket. The figure shows that a regular walk can generate very high acceleration values that appear like a landing shock, and can also generate very low acceleration values that may appear as free falls.

Vock, et al., also propose various methods for filtering out erroneous jump detections. In particular, they propose to filter jumps by velocity value or the length of the suspected jump.

These limitations are useful, but still not sufficient. Any hard threshold will be too small for some jumps and too large for some false alarms. As an example, velocity of a high speed ski lift is comparable with low speed skiing, and there is often a detectable shock when a skier gets on and off the lift chair. A hard jump duration limit is not very reliable either. For example, a snowboarder might have a series of small jumps when getting on and off rails and benches, and such jumps would not be reliably detected.

We conclude from the above examples that there is no one parameter that can reliably identify a jump, but rather there are a large number of very different parameters which must be considered in their interactions to make a reliable jump identification and air time measurement. However, trying to fit all of these parameters using thresholds and binary logic creates a decision algorithm that quickly becomes extremely complicated, and at some point it becomes virtually impossible to create an effective and manageable algorithm using binary logic and thresholds.

SUMMARY

It is an overall objective of this invention to provide a new and improved method and apparatus that overcomes one or more of the above problems and complications and allows efficient and reliable detection of the sport jumps and accurate measuring air time and high of the jumps. The current invention addresses how to detect and measure sportsman jumps in a reliable and efficient way.

A system and method for determining sportsman jumps and jump parameters such as airtime is presented. Accelerometer data generated by a sportsman's motion is received in a computing device. The computing device is used to apply fuzzy logic membership functions to a plurality of parameters associated with the accelerometer data to detect a pattern associated with jumps. A subset of the data is identified as representing a jump based upon the detection of the pattern. The determination is used in the computing device to transform data, whereby jumps are separated from other sportsman motion. The determination may further be based on the application of fuzzy logic membership functions to GPS sensor measurements. The use of fuzzy logic allows, in an embodiment, implementing very flexible and complex analysis rules that take into account the entire pattern of sensor response. The focus of the processing is to separate jumps from other sportsman activities that often produce very similar sensor signatures.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

DETAILED DESCRIPTION

Figure 1:
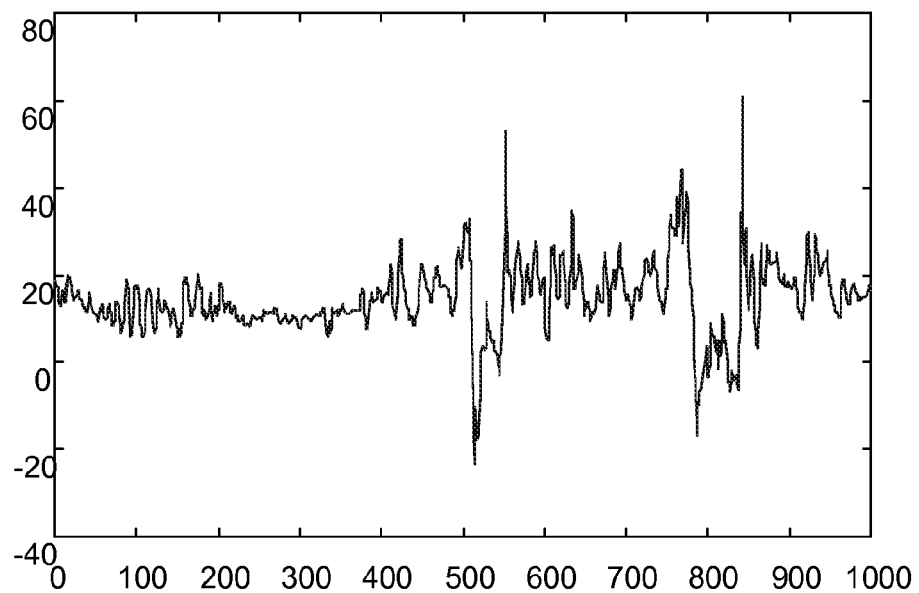
FIG. 1 shows a chart of the sum of three-axis accelerometer signals for a skier performing a downhill run with jumps.
Figure 2:
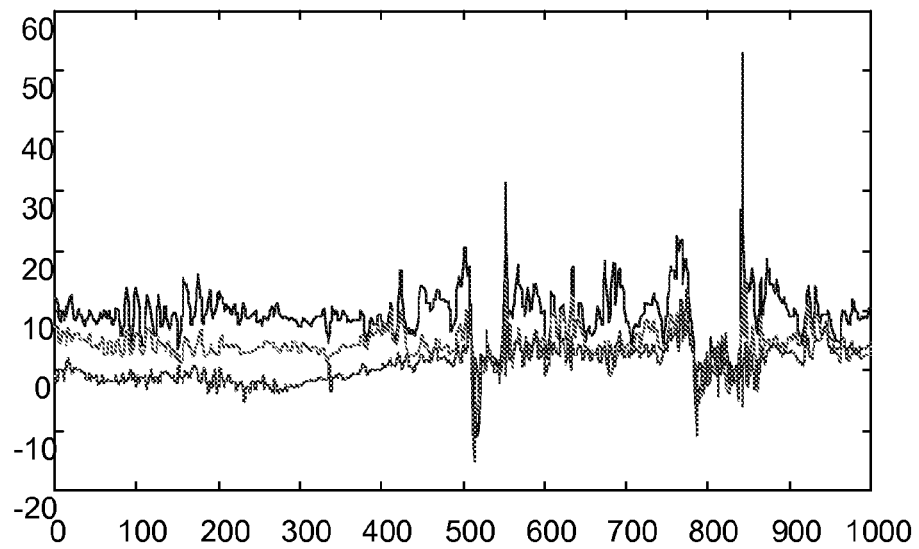
FIG. 2 shows a chart of individual three-axis acceleration signals for the run shown in FIG. 1.
Figure 3:
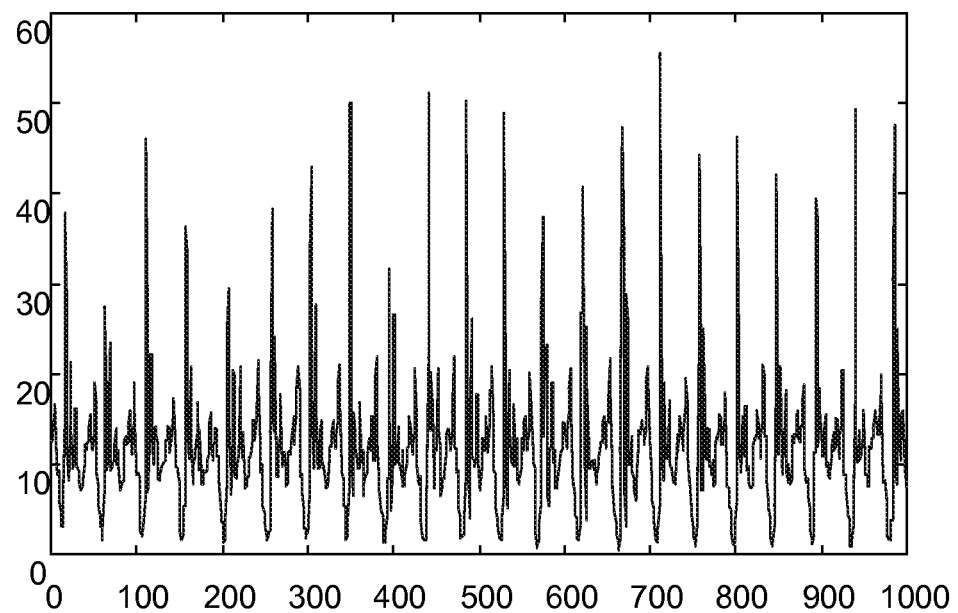
FIG. 3 shows a chart of an acceleration signal (acceleration vector norm) during walking.

Reference will now be made in detail to the preferred embodiments of the present invention, examples of which are illustrated in the accompanying drawings.

The present invention is described below with reference to block diagrams and operational illustrations of methods for determining jumps. It is understood that each block of the block diagrams or operational illustrations, and combinations of blocks in the block diagrams or operational illustrations, may be implemented by means of analog or digital hardware and computer program instructions. These computer program instructions may be stored on computer-readable media and provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

Selection of the Observable Parameters

It is known from basic physics that the major characteristic of a "free fall" condition is that any accelerometer rigidly attached to a body does not register any signal above its normal noise, when this body is in free fall. However, in practice, a sportsman's jump is not a truly a free fall condition due to rotation. Because of relative motion of different parts of the body relative to the center of mass, the accelerometers often show signals far exceeding their noise level during a jump. The situation becomes even more complicated in the case when sensors are not rigidly attached to the body, e.g. a cell phone freely positioned in a jumper breast pocket.

In accordance with an embodiment of the invention, a norm of a calibrated 3x axis accelerometer is used as an observable parameter:

$$A_{nrm} = \text{sqrt}(A_x^2 + A_y^2 + A_z^2)$$

Let acceleration vector A consist of a vertical component $A_g$ along the gravity direction, and a horizontal component $A_h$. Then vector norm $A_{nrm}$ can be expressed as:

$$A_{nrm} = \text{sqrt}(A_g^2 + A_h^2)$$

For jump detection we are most often only interested in the Ag component. Therefore, the effective SNR is:

$$SNR = A_g/A_{nrm} = 1/\text{sqrt}(A_h/A_g)^2)$$

It is clear that the main factor for jump detection is the acceleration component along a gravity vector. Unfortunately, it is very difficult to determine sensor absolute orientation during a jump. However, during a jump, readings of the magnetic vector are not affected. In most areas of North America, Earth magnetic vector points down 60-80 degrees from horizontal. Therefore, if we project the acceleration vector on the magnetic vector, then the vertical component of the acceleration will be relatively enhanced compared to its horizontal component:

$$Am = Ag*\cos(a) + Ah*\sin(a)$$

Where a is the angle between earth magnetic vector and the vertical.

Therefore, the SNR in this case is:

$$SNR = Ag*\cos(a)/Am = 1/(1+(Ah/Ag)*tg(a))$$

Figure 5:
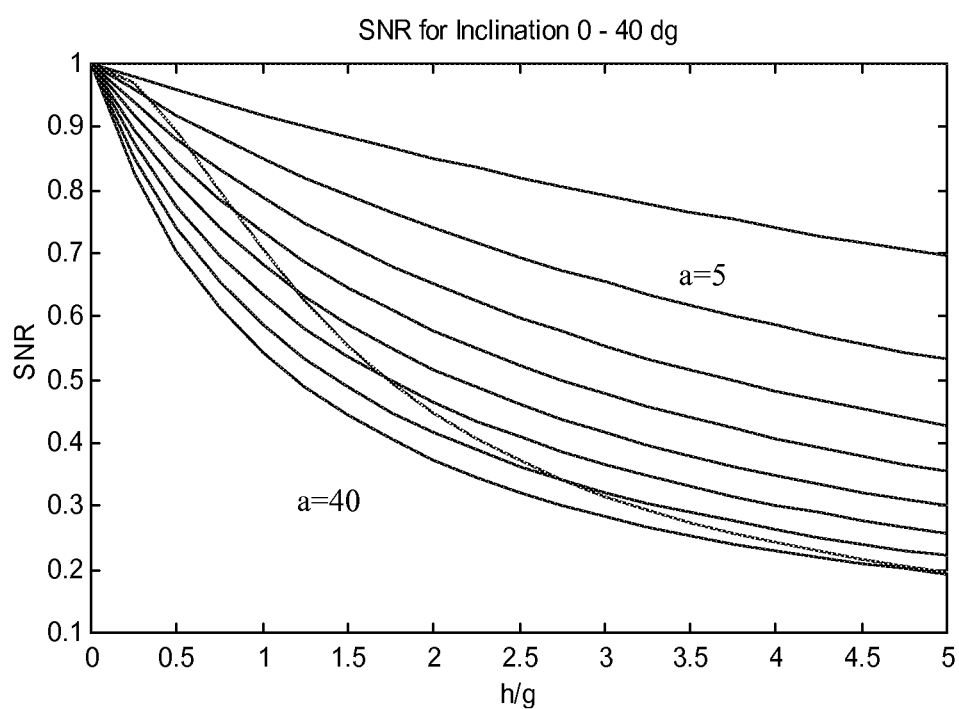
FIG. 5 shows a chart illustrating Signal-to-Noise Ratio (hereinafter "SNR") as a function of $A_h/A_g$ for different values of magnetic inclination (angle between Earth magnetic vector and vertical).

FIG. 5 shows how SNR varies with magnetic inclination angle, which is the angle between the Earth magnetic vector and the local vertical. As is illustrated in the drawing, an inclination below 30 degrees projection on the magnetic vector gives a better SNR than a vector norm of the acceleration. The value for inclination is well known, and can be tabulated or explicitly computed for any location on the Earth.

The present invention in one embodiment provides a system and method for determining a jump wherein, for locations where the Earth magnetic vector differs from the vertical by less than some value, a projection of the acceleration vector on the magnetic vector is used as an observable parameter.

Algorithm Description

As mentioned above, independent of what is used as an observable value, there is no unique parameter that allows detection of jumps. On the contrary, there are many different criteria that should be satisfied. For example, the norm of acceleration (or other observable parameter) should be "small enough" in some set of points, and this set should be "large enough" at another set of points due to a "large" acceleration after the jump that corresponds to landing, etc. The main problem for binary-logic-based and thresholds-based approaches is that all the rules that help to differentiate a "jump" from "not a jump" are intuitive and, more importantly, non-rigorous. Therefore, there is no rule for choosing "correct" values of thresholds. Moreover, a rigorous approach cannot be proposed in principle as all physics of the problem available from accelerometer readings are already taken into account. Thus the approach for jump detection should be rather more intuitive than rigorous.

Figure 4:
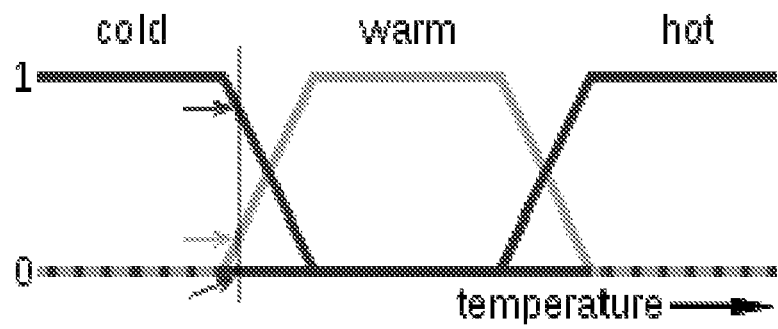
FIG. 4 shows a diagram illustrating a known fuzzy logic membership function example.

The approach that allows one to formulate intuitive rules in mathematical language is fuzzy logic, proposed by Zadeh, L. A., *Fuzzy Sets*//Inform. Contr. 8:338-53, 1965. The fuzzy logic approach is based on the concept of membership functions. A membership function MF describes a value from 0 to 1 that describes a level of belonging an object to a set (in contrast to binary logic, where the object can either belong to the set or not). A value of 0 indicates a state of not belonging to the set, whereas a value of 1 indicates a state of full belonging to the set, and any value in between represents how definitely an object belongs to the set. As an example, suppose part of a control algorithm is a need to determine if water is Cold, Warm, or Hot. See the article *Fuzzy Logic*, http://en.wikipedia.org/wiki/Fuzzy_logic. A traditional binary logic approach would be to set two hard thresholds, $T_{cold}$ and $T_{hot}$, and then make the following determinations:

if $T < T_{cold}$ then water is COLD
if $T > T_{hot}$ then water is HOT
if $T_{cold} <= T <= T_{hot}$ then water is WARM In contrast, fuzzy logic allows the assignment of a degree of "Coldness" or "Hotness" and then operating with these values. FIG. 4 shows an example of a membership function for these three sets—Cold, Warm, and Hot.

The present invention, in an embodiment, utilizes a fuzzy logic approach to jump detection. Such approach allows one to combine multiple and flexible conditions in a computable algorithm.

For demonstration purposes, we will use norm(ACC) vs. time as an observable variable. However, as discussed above, in some situations a projection of acceleration on the magnetic vector can be preferable.

Figure 6:
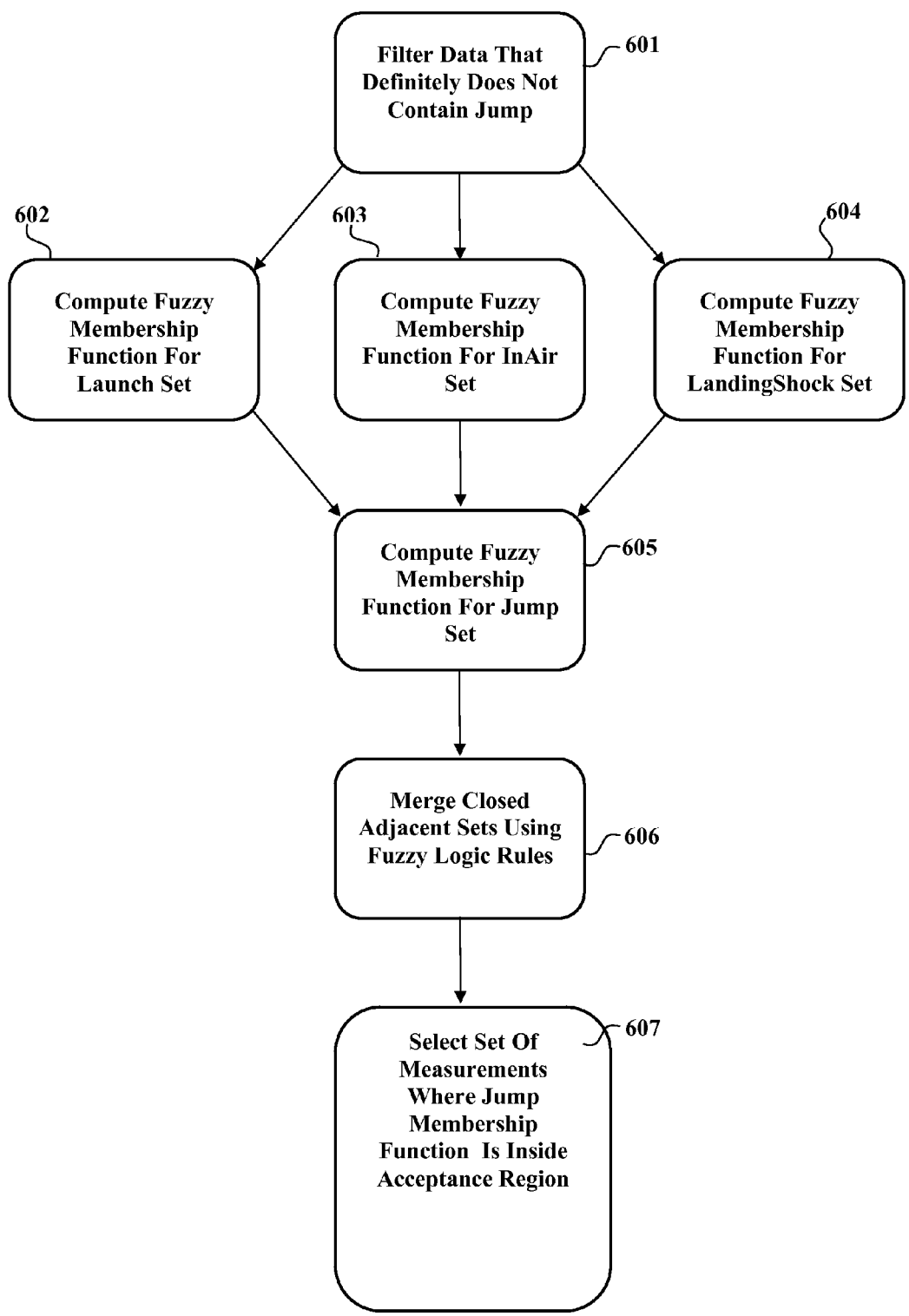
FIG. 6 shows a flow diagram illustrating steps for practicing the present invention in one embodiment thereof.

FIG. 6 shows a flow diagram illustrating a method for performing jump detection in accordance with one embodiment of the invention.

In step 601, data that definitely does not contain a jump is filtered. For snow sports jumps, detection should only be applied during the segment when the sportsman is moving downhill at relatively high speed. This can be accomplished by filtering out segments and data from when the sportsman is known or detected to be on a chairlift or moving with slow speed. In an embodiment, when chairlifts are known or detected, jumps can be searched only in the data records or data measurements where recorded or measured altitude is above the lowest lift altitude.

After the above filtering is applied, the main portion of the algorithm, based on fuzzy logic, is applied. First, the general concept will be described. Jumps are determined/identified among the selected records by taking into account the mutual relationship between three measurements sets, which we will call the Launch Set, the InAir Set, and the LandingShock Set for purposes of explanation. The Launch Set is a set of measurements where the sportsman is suspected to be springing up. The InAir Set is a set of measurements where the sportsman is suspected to be moving through the air without mechanical assistance and only due to the initial energy obtained during the launch stage. A LandingShock Set is a set of measurements which are suspected to be taken during the landing on snow, water, ground, or artificial obstacles such as rails, boxes, etc.

At steps 602, 603 and 604, for each measurement point, a fuzzy membership function is computed for each of the three sets respectively. Membership functions are computed using fuzzy logic rules. A measurement point's membership function values are computed based on the measurement fuzzy description of at least some of such parameters as Near Zero Acceleration, Low Acceleration, High Acceleration, Very High Acceleration, Wide set, Narrow set, Sharp Peak, Very Sharp Peak, High Velocity, Low velocity.

In step 605, the Jump Set membership function is computed from the membership functions of Launch, InAir, and LandingShock sets using fuzzy logic rules.

In step 606, closed adjacent sets are merged using fuzzy logic rules.

In step 607, a final determination/identification of a jump is made by selecting a set of measurements where the membership function Jump is within some predetermined acceptance region.

An object of the invention is to determine a jump by taking into consideration a large number of factors and their relative certainty. In other words, an accelerometer time record represents a jump if a composition of multiple criteria have high enough certainty all together. This can happen if some of the criteria are very high or, while each of the criteria is not definite, a summary of the many criteria is high, and the conditions of a "false jump" are not satisfied.

As a result, a combined membership function is computed, which can be compared against a length of the jump. Again, if instead of a harsh time-threshold condition such as "it is a jump if a time interval is larger than a curtain period" a membership function is used, this allows one to create a functional dependency between a value of the membership function and the jump duration. If membership function is high, then a shorter jump duration could be accepted, but for a small membership function, a larger time duration is required to declare a signal signature to be a jump.

Figure 7:
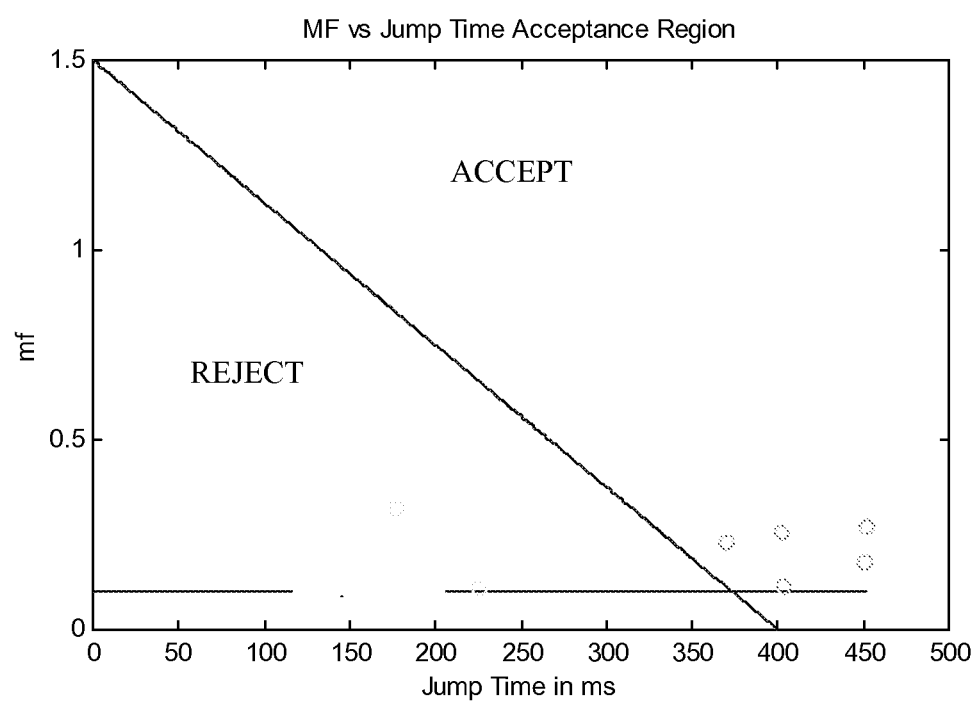
FIG. 7 shows a chart illustrating membership function vs. jump time acceptance region.

FIG. 7 shows an acceptance region in the (MF,T) space. Low membership functions are rejected, and to accept smaller jump time T a larger value of membership function is required.

Example Implementation

The following implementation demonstrates a possible use of fuzzy logic for jump determination. This example illustrates how fuzzy logic rules allow a combination of multiple requirements to be used without setting rigid thresholds and very complicated if-then statements.

Let us formulate the algorithm using fuzzy logic. As implementation of fuzzy logic is somewhat arbitrary (membership functions and logic operations are not unique), the fuzzy part of the algorithm is formulated in the form of fuzzy rules. A possible algorithm is given below:

accelerometer signals are normalized using known sensor bias and gain parameters.

If gyro sensors are available then accelerometer readings are corrected by an approximate centrifugal acceleration which is due to the sportsman rotation:

$$Ac = W \times (W \times R)$$

where W is angular velocity vector and R is an expected radius between the sensor device and the axis of rotation.

Compute vector norm of the calibrated and corrected 3x accelerometer signal:

$$An = \operatorname{sqrt}(ax^2 + ay^2 + az^2);$$

First of all one should determine "suspicious" points that belong to InAir set.

IF the norm of acceleration in the point is SMALL
THEN the point belongs to the InAir set.

Membership function mf_SmallAcc is used in order to determine smallness of acceleration. At the present step InAir membership function is set to be equal to mf_SmallAcc. After this procedure the data will be divided into several sets of suspicious points (where InAir membership function is not equal to zero).

Initial merging is applied to all points. If both neighbors of the point have non-zero membership function InAir then membership function in the point is calculated as average value of membership function in the neighboring points.

The following rule are used in order to determine whether two neighboring InAir sets should be merged:

IF
  1) the distance between two neighboring SETs is small
AND
  2) there is no large acceleration between SETs
AND
  3) both SETs contain very small accelerations
OR
  4) mean acceleration in both SETs is small
THEN
  points between two sets also belong to InAir set.

InAir membership function for points between two merging sets is calculated as average value of InAir membership in the boundary points of merging sets.

The next step is used in order to prevent false alarms

IF
  1) the InAir set includes at least one point with very small acceleration
AND
  2) mean acceleration over the set is small
THEN
  the set is a true InAir set.
ELSE
  InAir membership function is set to zero in all points of the set.

The next step is to check all InAir sets and decide whether each set can be considered as a jump or not using the following IF-THEN rules:

IF
  1) the set is not small
AND
  2) there is a SHOCK on the right from the set. The SHOCK is a point that is simultaneously the closest to the set
AND
  the largest (norm of acceleration is the largest)
AND
  the sharpest (acceleration has a peak in this point)
THEN
  the set can be considered as a jump.

In the present above step the InAir membership function is combined with membership functions that characterize presence of shock and size of the set itself.

Determine Jump Duration:

For all sets with MF>0 define jump width W as the width of the set.

Then, the final decision is made. In this step, a set is considered a Jump if a corresponding point (MF,W) is located inside the Acceptance Region (as shown in FIG. 7.)

Thus, the algorithm shown above takes into account many different parameters characterizing jump. The main part of the algorithm is based on fuzzy logic. The only non-fuzzy rule is used in the very end in order to make the final decision.

After a jump is detected, its length (time duration) is set to the time length of the corresponding MF set.

When jump duration is determined, the jump height can be determined from a well known physics relationship:

$$T\text{up} = V0\text{up}/g;$$

$$H = g*(T\text{jmp} - T\text{up})^2/2$$

Here, V0up is a vertical velocity at the beginning of the jump.

All processing steps described herein, and particularly the fuzzy logic processing steps, may be performed on a computing device that is part of a portable data collection device carried by the sportsman. For example, such portable data collection device may be a portable computing device or smartphone with an accelerometer therein. Such computing device comprises, e.g., a processor for carrying out instructions; computer readable media such as static memory and/or dynamic memory for storing computer program instructions; input means such as a touch screen, keyboard, voice input, mouse, or the like; a network interface for communicating over a wireless and/or wired network, and a user interface such as a display, speaker, and hard or soft buttons. The portable data collection device further includes an accelerometer, such as a three-axis accelerometer, and may also include a GPS receiver and the capability to determine its position using the same. Alternatively, or in addition, all processing steps described herein, and particularly the fuzzy logic processing steps, may be performed on a computing device that is remote from the portable data collection device. For example, a remote server or remote desktop computer may be provided and receive process raw or preprocessed accelerometer data from the portable data collection device. The transmission of data from such portable data collection device to the remote computing device may be performed via a wireless and/or wired network interface associated with the portable data collection device and a wireless and/or wired network interface associated with the remote server or remote desktop computer.

The above embodiments and preferences are illustrative of the present invention. It is neither necessary, nor intended for this patent to outline or define every possible combination or embodiment. The inventor has disclosed sufficient information to permit one skilled in the art to practice at least one embodiment of the invention. The above description and drawings are merely illustrative of the present invention and that changes in components, structure and procedure are possible without departing from the scope of the present invention as defined in the following claims. For example, elements and/or steps described above and/or in the following claims in a particular order may be practiced in a different order without departing from the invention. Thus, while the invention has been particularly shown and described with reference to embodiments thereof, it will be understood by those skilled in the art that various changes in form and details may be made therein without departing from the spirit and scope of the invention.

What is claimed is:

1. A method comprising:
   receiving, by a computing device, accelerometer data generated by a sportsman's motion from an accelerometer coupled to the sportsman and in communication with the computing device;
   applying, by the computing device, a plurality of fuzzy logic membership functions to a plurality of parameters associated with the accelerometer data to detect a pattern associated with a jump, wherein detection of the pattern associated with the jump includes:
      determining a fuzzy logic initial jump probability membership function;
      determining a fuzzy logic jump start probability membership function;
      determining a fuzzy logic landing shock probability membership function;
      determining a fuzzy logic false jump probability membership function; and
      combining the jump start probability and landing shock probability membership functions together using fuzzy logic rules;
   identifying a subset of the accelerometer data representing the jump based upon the detected pattern; and
   transforming the accelerometer data, by the computing device, by separating the identified subset of accelerometer data representing the jump from accelerometer data associated with other motion by the sportsman.

2. The method of claim 1, further comprising:
   receiving, by the computing device, global positioning sensor (GPS) measurements from a GPS device coupled to the sportsman and in communication with the computing device; and
   identifying the subset of the accelerometer data representing the jump based at least in part on the received GPS measurements.

3. The method of claim 2, wherein the fuzzy logic membership functions are applied to the GPS measurements to detect the pattern associated with the jump.

4. The method of claim 1, wherein a time duration of the jump of the sportsman is further determined.

5. The method of claim 3, wherein acceptance and rejection are mapped as 2D regions on a membership function vs. a jumptime plane.

6. The method of claim 4, wherein a total norm of a 3x axis accelerometer is used.

7. The method of claim 4, wherein a projection of an accelerometer vector to the magnetic vector is used.

8. The method of claim 4, wherein accelerometer data is collected only in response to the computing device measuring a velocity of the sportsman above some predetermined threshold.

9. The method of claim 6, wherein the accelerometer data is corrected by an approximate rotational acceleration computed from gyro sensors coupled to the sportsman and in communication with the computing device.

10. The method of claim 1, wherein the accelerometer data is time tagged.

11. The method of claim 1, wherein the computing device comprises a smartphone with an accelerometer therein.

12. A non-transitory computer readable storage medium storing instructions that, when executed by a computing device, cause the computing device to:
   receive accelerometer data generated by a sportsman's motion from an accelerometer coupled to the sportsman and in communication with the computing device;
   apply a plurality of fuzzy logic membership functions to a plurality of parameters associated with the accelerometer data to detect a pattern associated with a jump, wherein detection of the pattern associated with the jump includes:
      determining a fuzzy logic initial jump probability membership function;
      determining a fuzzy logic jump start probability membership function;
      determining a fuzzy logic landing shock probability membership function;
      determining a fuzzy logic false jump probability membership function; and
      combining the jump start probability and landing shock probability membership functions together using fuzzy logic rules;
   identify a subset of the accelerometer data representing the jump based upon the detected pattern; and transform the accelerometer data by separating the identified subset of accelerometer data representing the jump from accelerometer data associated with other motion by the sportsman.

* * * * *

UNITED STATES PATENT AND TRADEMARK OFFICE
CERTIFICATE OF CORRECTION

| | | |
|---|---|---|
| PATENT NO. | : 9,326,704 B2 | Page 1 of 1 |
| APPLICATION NO. | : 13/612470 | |
| DATED | : May 3, 2016 | |
| INVENTOR(S) | : Lokshin et al. | |

It is certified that error appears in the above-identified patent and that said Letters Patent is hereby corrected as shown below:

In the specification

In Column 1, Line 38, delete "when he" and insert -- when the --, therefor.

In Column 5, Line 16, delete "SNR=$A_g/A_{nrm}$=1/sqrt($A_h/A_g$)²)" and insert -- SNR = $A_g/A_{nrm}$ = 1/sqrt(1 + ($A_h/A_g$)²) --, therefor.

Signed and Sealed this
Ninth Day of August, 2016

Michelle K. Lee
*Director of the United States Patent and Trademark Office*